United States Patent
Like

(10) Patent No.: US 6,339,056 B1
(45) Date of Patent: Jan. 15, 2002

(54) AMMONIA BASED CLEANING AND DISINFECTING COMPOSITION

(75) Inventor: Burton M. Like, East Brunswick, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 09/360,913

(22) Filed: Jul. 26, 1999

(51) Int. Cl.[7] .............................. C11D 1/62; C11D 3/48
(52) U.S. Cl. ..................... 510/383; 510/243; 510/319; 510/382; 510/384; 510/391; 510/435; 510/480; 510/504; 510/509
(58) Field of Search ................ 510/243, 319, 510/382, 384, 391, 435, 480, 509, 504, 383

(56) References Cited

U.S. PATENT DOCUMENTS

| | | | | |
|---|---|---|---|---|
| 4,174,304 A | * | 11/1979 | Flanagan | 252/524 |
| 4,343,725 A | * | 8/1982 | Kiewert et al. | 252/542 |
| 4,559,151 A | * | 12/1985 | Pregozen et al. | 252/8.8 |
| H269 H | * | 5/1987 | Malik | 422/37 |
| 4,784,789 A | * | 11/1988 | Jeschke et al. | 252/174.23 |
| 4,822,514 A | * | 4/1989 | Becker | 252/108 |
| 5,389,685 A | | 2/1995 | Smith et al. | 514/643 |
| 5,435,935 A | | 7/1995 | Kupneski | 252/156 |
| 5,454,983 A | | 10/1995 | Michael et al. | 252/545 |
| 5,507,971 A | * | 4/1996 | Ouzounis et al. | 252/174.24 |
| 5,585,341 A | * | 12/1996 | Van Eenam | 510/365 |
| 5,714,453 A | * | 2/1998 | Neumiller | 510/405 |
| 5,767,054 A | | 6/1998 | Sprugel et al. | 510/383 |
| 5,849,681 A | * | 12/1998 | Neumiller et al. | 510/182 |

* cited by examiner

Primary Examiner—Charles Boyer
(74) Attorney, Agent, or Firm—Irving M. Fishman, Esq.

(57) ABSTRACT

A disinfecting cleaning composition comprising an aqueous solution of a cleansing amount of ammonia which results in the removal of a significant amount of soils and stains when applied to a surface after appropriate dilution, and an amount of a biocidal, nonampholytic quaternary ammonium salt (quat) which is less than that necessary to achieve complete disinfection after dilution in the absence of ammonia.

27 Claims, No Drawings

AMMONIA BASED CLEANING AND DISINFECTING COMPOSITION

SEQUENCE LISTING

Not Applicable

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The invention relates to ammonia based household cleansers which have a disinfecting effect on harmful microorganisms.

2. Background Information Including Description of Related Art

Aqueous ammonia based household cleansers are a well-known product of commerce. However, despite a possible public misconception due to the pungent odor of these cleansers, they ordinarily do not exert any substantial disinfecting effect with regard to harmful microorganisms on the surfaces to which they are applied. Thus, in view of the public's desire for disinfection generally in many different applications, any modification of an ammonia based household cleanser which causes the ammonia contained therein to have some disinfecting effect would be very desirable.

U.S. Pat. No. 5,389,685, issued Feb. 14, 1995 to Smith et al., discloses disinfectant compositions comprising an aqueous solution of a bacteriocidal quaternary ammonium compound and an alkali bicarbonate, e.g., sodium bicarbonate.

U.S. Pat. No. 5,435,935, issued Jul. 25, 1995 to Kupneski; U.S. Pat. No. 5,454,983, issued Oct. 3, 1995 to Michael et al.; and U.S. Pat. No. 5,767,054, issued Jun. 16, 1998 to Sprugel et al., each shows surface cleaning and disinfect compositions comprising a quaternary ammonium halide disinfectant and ammonia as a buffering agent.

U.S. Pat. No. 5,849,681 issued Dec. 15, 1998 to Neumiller et al., discloses glass cleaning compositions with enhanced anti-streaking properties comprising a hydroxy substituted ether and an anti-streaking alcohol. The composition may also contain a quaternary ammonium salt as an antimicrobial and/or disinfectant compound and other "conventional" materials such as ammonia. Among seven examples and seven comparative examples containing ammonia shown in the patent, the largest amount of ammonia disclosed is in the composition of Comparative Example 8, which contains 1.00 wt. % of 28.5% ammonia or an overall amount of ammonia of 0.285 wt. %.

U.S. Statutory Invention Reg. No. H269 of Malik, published May 5, 1987, discloses disinfectant cleaner compositions comprising a germicidal quaternary ammonium halide and a glycoside surfactant, and may also contain ammonia as a "discretionary" or "supplemental or auxiliary" ingredient.

BRIEF SUMMARY OF THE INVENTION

In accordance with this invention, a cleaning composition for surfaces is provided comprising an aqueous solution of a cleansing amount of ammonia, i.e., an amount resulting in the removal of a significant amount of soils and stains when applied to a surface after appropriate dilution, and an amount of a biocidal, non-ampholytic quaternary ammonium salt (quat.) which is less than that necessary to achieve complete disinfection after said dilution in the absence of ammonia. Although ammonia is known to have little or no disinfecting effect when present in cleaning compositions, it has been found that the combination of ammonia in amounts used in cleaning compositions with a biocidal quat. in an amount less than that necessary to obtain complete disinfection after appropriate dilution, surprisingly results in a composition having a substantially greater disinfecting effect than a composition containing the same amount of quat. but no ammonia. In many cases, use of the composition containing amounts of ammonia and quat. as described results in complete disinfection of the cleaned surface.

BRIEF DESCRIPTION OF THE SEVERAL VIEWS OF THE DRAWINGS

Not Applicable

DETAILED DESCRIPTION OF THE INVENTION

In the following description and claims, all the percentages are weight percentages based on the total weight of the composition, unless otherwise defined.

The compositions of this invention contain an amount of ammonia sufficient to exert a significant cleaning effect after appropriate dilution on the surface to which the diluted composition is applied. In many cases, the amount of ammonia in the composition will be, for example, about 0.5 to about 10 wt. %, preferably about 1.0 to about 5.0 wt. %. While at least some of the ammonia dissolved in water is believed to be in the form of ammonium hydroxide, the foregoing percentages are based on an assumption of pure ammonia ($NH_3$), as the solute.

The biocidal quats contemplated under this invention are well known in the art. They are composed of one or more single charged cations each made up of a central nitrogen atom bonded to four organic groups of various types, electrostatically coupled with the anion of a strong acid. Preferably, two of the organic groups bonded to the nitrogen are methyl, one of the organic groups bonded to the nitrogen is a long chain alkyl, e.g., n-alkyl, containing about 8 to about 24, more preferably about 8 to about 18 carbon atoms, and one of the organic groups is either methyl, said long chain alkyl, benzyl, or alkylbenzyl wherein an alkyl group containing, e.g. 1 to 4 carbon atoms is bonded to a ring carbon atom of a benzyl group. Each long chain alkyl as defined may be single valued, i.e., may be the same among substantially all the quat. molecules, or may be a mixed alkyl made up of different alkyls containing varying numbers of carbon atoms in the range of about 8 to about 24 among the quat. molecules. Moreover, if the quat. contains two long chain alkyl groups bonded to the nitrogen atoms, they may be the same or different among the single valued or mixed alkyl groups as defined. Mixtures of quats containing different organic groups bonded to nitrogen as previously described, may be used. The preferred quats among all the foregoing categories are the quaternary ammonium halides, and most preferred are the quaternary ammonium chlorides, among which are mixed $Cl_2$–$Cl_6$ n-alkyl dimethyl benzyl ammonium chloride; n-octyl n-decyl dimethyl ammonium chloride; di-n-octyl dimethyl ammonium chloride; di-n-decyl dimethyl ammonium chloride; mixed $C_{12}$–$C_{18}$ n-alkyl dimethyl benzyl ammonium chloride; and mixed $C_{12}$–$C_{14}$ n-alkyl dimethyl ethylbenzyl ammonium chloride. The quat. may be added to the composition as the pure salt or it may be mixed with inert ingredients, e.g., in an amount of 20 to 50 wt. % of the total quat. composition, for better dissolution and compounding.

A preferred class of active quats. are those consisting of about 30 to about 50 wt. % of at least one long chain n-alkyl dimethyl benzylamonium chloride and about 50 to about 70 wt. % of at least one di(long chain alkyl) dimethyl ammonium chloride, most preferably the specific quat utilized in Examples 1 and 2 and Comparative Examples A and B as described hereinafter.

Another preferred class of active quats. are those consisting of about 40 to about 60 wt. % of at least one long chain n-alkyl dimethyl benzyl ammonium chloride and about 40 to about 60 wt. % of at least one long chain n-alkyl dimethyl ethylbenzyl ammonium chloride, most preferably the specific quat utilized in Example 9 as described hereinafter.

The total active quat. in the composition is present in an amount which is generally less than that which would effect complete disinfection at an appropriate dilution ratio when present in the same composition except that no ammonia is present. Such amount before dilution is in the range, for example of about 0.4 to about 1.6 wt. %, preferably about 0.6 to about 1.0 wt. % based on the weight of the composition. After dilution, the composition may contain, for example, about 100 to about 1000 ppm of pure quat. at a dilution ratio of about 1:16 to about 1:32.

The aqueous cleaning composition of the invention also advantageously contains a nonionic surfactant. Specific nonionic surfactants which can be used include ethoxylated fatty alcohols, preferably linear primary or secondary monohydric alcohols with $C_{10}$–$C_{18}$, preferably $C_{12}$–$C_{16}$, alkyl groups and on average about 1–15, preferably 3–12 moles of ethylene oxide (EO) per mole of alcohol, and ethoxylated alkylphenols with $C_8$–$C_{16}$ alkyl groups, preferably $C_8$–$C_9$ alkyl groups, and on average about 4–12 moles of EO per mole of alkyl phenol.

The preferred class of nonionic surfactants are the ethoxylated linear alcohols, such as the $C_{12}$–$C_{16}$ alcohols ethoxylated with an average of from about 3 to about 12 moles of ethylene oxide per mole of alcohol. A most preferred nonionic detergent is a $C_{12}$–$C_{14}$ alcohol ethoxylated with 7 moles of ethylene oxide per mole of alcohol.

The amount of nonionic surfactant in the composition is, for example, about 0.2 to about 10.0 wt. %, preferably about 0.5 to about 2.5 wt. %, based on the total weight of the composition. Preferably the composition does not contain any anionic surfactant, since anionic surfactants may be incompatible with the contemplated quat.

Certain chelating agents not incompatible with the quat. may also be present for the purpose of sequestering undesirable metallic ions, particularly iron which tends to be leached out from metallic surfaces by aqueous ammonia and may cause undesirable discoloration of the composition. Such chelating agents include, for example, the trisodium salt of N-hydroxyethylethylenediamine triacetic acid, triethanolamine, and sodium gluconate, each of which may be present in an amount of from about 0.01 to about 0.5 wt. %

The composition of this invention may also contain, as a color stabilizer and buffer, an alkaline bicarbonate, preferably an alkali metal bicarbonate, and most preferably sodium bicarbonate (SBC). If used, the alkaline bicarbonate may be present in an amount in the range of about 0.1 to about 5.0 wt. %, preferably about 0.5 to about 3.0 wt. %.

Other optional ingredients may also be present as are well-known in the art, including fragrance oils, colorants, optical brighteners, UV absorbents, enzymes, etc. The total of these additional optional materials may be within the range, for example, of about 0.1 to about 2.0 wt. %.

The balance of the composition in which all the foregoing ingredients are dissolved or dispersed, is water which may be present in an amount, for example, of about 69 to about 98 wt. %, preferably about 86 to about 97 wt. %. Preferably, the ingredients are dissolved or very finely dispersed in the water, so that the composition has a clear appearance.

The following examples further illustrate the invention.

EXAMPLES 1 AND 2 AND COMPARATIVE EXAMPLES A, B AND C

To test the disinfecting effect of compositions within the invention (Examples 1 and 2) containing both ammonia and a quat. under the invention, as compared with compositions outside the invention (Comparative Examples A, B and C) containing either the same quat. or ammonia in the same quantities as Examples 1 and 2, but not both, compositions were prepared containing various combinations of the following ingredients: ammonia as a 29 wt. % aqueous solution ($NH_3$, 29%); a quaternary ammonium salt additive (Quat, 50%) composed of about 20 wt. % (40 wt. % of active quat.) of a long chain n-alkyl dimethyl benzyl ammonium chloride wherein the long chain n-alkyl group is a mixed alkyl composed of about 50 wt. % of $C_{14}$, 40 wt. % of $C_{12}$, and 10 wt. % of $C_{16}$, based on the total weight of n-alkyl, about 15 wt. % (30 wt. % of active quat.) of n-octyl n-decyl dimethyl ammonium chloride, about 7.5 wt. % (15 wt. % of active quat.) of di-n-octyl dimethyl ammonium chloride, about 7.5 wt. % (15 wt. % of active quat.) of di-n-decyl dimethyl ammonium chloride, and 50 wt. % of inert ingredients, the percentages of each salt and inert ingredients based on the total weight of the quat. additive as received, such 50% quat. additive sold by the Stepan Company under the registered trademark "BTC 885"; as a nonionic surfactant (Nonionic Surf.), an ethoxylated $C_{12}$–$C_{14}$ n-alkanol containing an average of 7 ethoxy groups per mole of n-alkanol and sold by Huntsman under the trademark "Surfonic L24-7; as iron sequestering chelating agents, triethanolamine (TEA) and the trisodium salt of N-hydroxyethylethylenediaminetriacetic acid, sold by Dow Chemical Co. under the trademark "Versonal 120" (Versonal 120); fragrance TF14170 (Fragrance) sold by Givaudan-Poure; olive dye LX-5385 as a 1.0% solution (Dye, 1%); sodium bicarbonate (SBC); and water. The makeup of the compositions of the various examples in weight percentages of ingredients is shown in Table I.

TABLE I

| Example | 1 | 2 | A | B | C |
| --- | --- | --- | --- | --- | --- |
| $NH_3$, 29% | 6.40 | 6.40 | 0 | 0 | 6.40 |
| Quat. 50% | 1.60 | 1.60 | 1.60 | 1.60 | 0 |
| Nonionic Surf. | 1.00 | 1.00 | 1.00 | 0 | 0 |
| TEA | 0.08 | 0.08 | 0.08 | 0 | 0 |
| Versonal 120 | 0.06 | 0.06 | 0.06 | 0 | 0 |
| Fragrance | 0.16 | 0.16 | 0.16 | 0 | 0 |
| Dye 1% | 0.19 | 0.19 | 0.19 | 0 | 0 |
| SBC | 0 | 0.50 | 0 | 0 | 0 |
| Water | 90.51 | 90.01 | 96.91 | 98.40 | 93.60 |

As can be seen in Table I, the compositions of Examples 1 and 2 under the invention contain a cleaning amount of ammonia and an amount of quat. which will be shown not to provide complete disinfection after 1/32 dilution in the absence of ammonia, together with other conventional ingredients, with the composition of Example 2 also containing 0.5 wt. % of SBC; the composition of comparative Example A is similar to that of Example 1 but without any ammonia; and comparative Examples B and C contain only quat. or ammonia respectively dissolved in water, without any of the other ingredients of Example 1 and 2 and Comparative Example A.

The disinfectant efficacies of the foregoing compositions were tested against various microorganisms obtained from the American Type Culture Collection (ATCC) and identified by ATCC number, by subjecting each composition to the Association of Official Analytical Chemists (AOAC) Use Dilution Screen Testing, the procedure for which is as follows:

Test specimens were prepared from culture suspensions of the following four microorganisms obtained from the ATCC and identified by ATCC number.

| | |
|---|---|
| Escherichia coli | (ATCC 11229) |
| Salmonella choleraesuis | (ATCC 10708) |
| Staphylococcus aureus | (ATCC 6538) |
| Pseudomonas aeruginosa | (ATCC 15442) |

Initially, stainless steel penicylinders (O.D. 8 mm±1) were presoaked overnight in 1N NaOH and washed in water. The penicylinders were autoclaved in asparagine at 15 psi at 121–124° C. for not less than 20 minutes, and stored in an incubator at 36±1° C. prior to test.

To prepare the culture specimen for testing, one set of 30 stainless steel penicylinders were transferred using a flamed and cooled nichrome wire hook to a 25×150 mm test tube containing 30 ml of the culture suspension, and were allowed to stand for 15 minutes at room temperature. After 15 minutes, the penicylinders were aseptically removed and placed in glass petri dishes matted with two pieces of Whatman No. 2 filter paper (5 penicylinders per petri dish), placing the penicylinders in an upright position. Inoculated penicylinders were placed into a 36±1° C. incubator for 40±5 minutes.

The test composition was applied to the microorganism at one cup/gallon (1/16) or ½ cup/gallon (1/32) dilution in sterile deionized water. Testing was performed by transferring one inoculated and dried penicylinder, at 20±2 second intervals into a 25×150 mm test tube containing 10 ml of diluted test composition maintained at 20±1° C. This process was continued until a set of 30 penicylinders were treated.

At the end of 10 minutes, each penicylinder was transferred, again at 20±2 second intervals, to one 10 ml test tube of Letheen Broth (a 5% sterile horse serum) per penicylinder (primary subculture). The subculture tubes of Letheen Broth (primary) were incubated at 36±1° C. for not less than 48 hours and observed for the presence or absence of visible growth (tubidity).

The foregoing procedure was repeated with the disinfectant ammonia cleanser of Example 1 or 2, one of the four specified microorganisms, and a sample dilution of 1/16 or 1/32, with the specific combinations of conditions being shown in Table II. Each test included 30 specimens as described.

TABLE II

| Composition Example | Organism | Sample Dilution, V/V |
|---|---|---|
| 1 | S. aureus | 1/16 |
| 1 | S. aureus | 1/32 |
| 1 | S. choleraesuis | 1/32 |
| 1 | P. aeruginosa | 1/32 |
| 1 | E. coli | 1/32 |
| 2 | P. aeruginosa | 1/32 |
| 2 | S. aureus | 1/16 |
| 2 | S. aureus | 1/32 |

In each of the tests, none of the 30 tubes containing Letheen Broth and primary subculture exposed to the diluted disinfectant ammonia composition of the invention exhibited any sign of visible growth indicated by turbidity. Thus, the composition under the invention achieved complete disinfection under the described conditions, as indicated by the AOAC Use-Dilution Screen Test which is a standard test of the art.

The AOAC Use-Dilution Screen Test as described was also carried out on the compositions of Comparative Examples A, B and C using Pseudomonas aeruginosa as the microorganism and a dilution ration of 1/32. The conditions and results of the test are shown in Table III.

TABLE III

| Composition Example | No. of Tubes Showing Growth |
|---|---|
| A | 12 |
| B | 12 |
| C | 30 |

Thus, the composition of Comparative Example A which was similar to that of Example 1 except that it contained no ammonia, and the composition of Comparative Example B which consisted of the same amount of quat. present in the composition of Example 1 dissolved in water, each resulted in 12 out of the 30 tubes showing visible growth (turbidity) when subjected to AOAC Use Dilution Screen Test as described, indicating only partial or spotty disinfection effected by the compositions after dilution, while the composition of Comparative Example C, which consisted of a solution of the same amount of ammonia present in the composition of Example 1 dissolved in water, resulted in all 30 of the tubes showing visible growth (turbidity) when subjected to the AOAC Test, indicating little or no disinfection effected by the composition after dilution. The results shown in Table II and III considered as a whole thus exhibit an unexpected synergistic disinfecting effect exerted by the quat. and ammonia since the disinfecting effect of the composition of Example 1 is greater than the additive disinfecting effects of the composition of Comparative Example A or B, which contains ammonia but no quat., and the composition of Comparative Example C which contains quat. but no ammonia. An advantage of this synergistic effect is that although ammonia itself does not exhibit any disinfecting effect, a completely disinfectant composition containing a cleansing amount of ammonia and quat. as the disinfectant agent, can be produced which contains a smaller amount of quat. than a completely disinfectant composition containing the same quat. as a disinfectant agent but no ammonia.

EXAMPLES 4 to 9 AND COMPARATIVE EXAMPLE D

These examples illustrate the inventive compositions utilizing different quats. in varying amounts, and a varying amount of nonionic surfactant.

The cleaning composition of each example contained 6.80 wt. % of an aqueous solution of 29 wt. % of ammonia, 0.06 wt. % of Versonal 120 chemically identified in Example 1 and 2, 0.08 wt. % of triethanolamine (85%), 0.15 wt. % of Fragrance 6539-HAY, 0.40% of FD&C Green #8 (1.0%) colorant, and 0.20 wt. % of FD&C Red #3 (0.1%) colorant. In addition, the compositions contained varying amounts of different quats. (Quat., 50%) and of Surfonic L24-7 nonionic surfactant (Nonionic Surf.) chemically identified in Examples 1 and 2, and water, as shown in Table IV.

The active quat. in Examples 3 to 6 was the same as that employed in Examples 1 and 2.

The quat. additive employed in Example 7 was composed of about 25.0 wt. % (50 wt. % of active quat.) of n-octyl n-decyl dimethyl ammonium chloride, about 12.5 wt. % (25 wt. % of active quat.) of di-n-octyl dimethyl ammonium chloride, about 12.5 wt. % (25 wt. % of active quat.) of di-n-decyl ammonium chloride, and 50 wt. % of inert ingredients, sold as "BTC 818" by Stepan Co.

The quat. additive employed in Example 8 was composed of about 50 wt. % (100 wt. % of active quat.) of long chain n-alkyl (50 wt. % $C_{14}$, 40 wt. % $C_{12}$ and 10 wt. % $C_{16}$) dimethyl benzyl ammonium chlorides, and about 50 wt. % of inert ingredients, sold as "BTC 835" by Stepan Co.

The quat. additive employed in Example 9 was composed of about 25 wt. % (50 wt. % of active quat.) of long chain n-alkyl (60 wt. % $C_{14}$, 30 wt. % $C_{16}$, 5 wt. % $C_{12}$ 5 wt. % $C_{18}$) dimethyl benzyl ammonium chloride, about 25 wt. % (50 wt. % active quat.) of long chain n-alkyl (68 wt. % $C_{12}$, 32 wt. % $C_{14}$) dimethyl ethylbenzyl ammonium chloride, and about 50 wt. % of inert ingredients, sold as "BTC 2125M" by Stepan Co.

The compositions of the examples were subjected to disinfection tests as described in Examples 1 and 2 and Comparative Examples A, B, and C using Pseudomonas aeruginosa as the test organism, and 1:32 dilution, except that 10 rather than 30 penicylinders were employed for each test. Variations in the compositions and the disinfection test results for these examples are shown in Table IV.

TABLE IV

| Example | Quat., 50% wt. % | Nonionic Surf., wt. % | Water wt. % | No. of Tubes Showing Growth |
|---|---|---|---|---|
| 3 | 1.60 | 1.00 | 89.71 | 0 |
| 4 | 1.20 | 1.00 | 90.11 | 1 |
| 5 | 0.80 | 1.00 | 90.51 | 3 |
| 6 | 1.60 | 4.00 | 86.71 | 2 |
| 7 | 1.60 | 1.00 | 89.71 | 0 |
| 8 | 1.60 | 1.00 | 89.71 | 4 |
| 9 | 1.60 | 1.00 | 89.71 | 0 |
| D | 0 | 1.00 | 91.31 | 10 |

The numbers shown in Table IV show that while the on of Example 3 containing 1.6 wt. % of 50% quat. and 6.80 of 29% ammonia, results in complete disinfection (no tubes showing growth), a composition having the same formula except that no quat. is present results in no disinfection at all (10 tubes showing growth). This is further indication that ammonia alone i.e. with quat., has no disinfection effect. It should be noted also that while the results of Examples 4, 5, 6 and 8 indicated less than complete disinfection caused by the indicated compositions, the degree of disinfection was in all cases greater than that which would result from the use of an otherwise identical composition containing the same amount of quat., except that no ammonia is present.

I claim:

1. A disinfecting cleaning composition comprising an aqueous solution of a cleansing amount of ammonia in the range of from 1.0 to about 5.0 wt. % which results in the removal of a significant amount of soils and stains when applied to a surface after appropriate dilution, and an amount of at least one biocidal, non-ampholytic quarternary ammonium salt (quat), in the range of about 0.4 to about 1.6 wt. % of the total composition.

2. The composition of claim 1 wherein said quat or each quat if more than one is present is a quaternary ammonium halide.

3. The composition of claim 2 wherein said quat or each quat if more than one is present is a quaternary ammonium chloride.

4. The composition of claim 3 wherein the quaternary ammonium chloride has a central nitrogen atom bonded to four organic groups of various types, two of the organic groups bonded to the nitrogen atom are methyl, one of said organic groups is a long chain alkyl, and one of said organic groups is long chain alkyl, benzyl or alkylbenzyl.

5. The composition of claim 4 wherein each of said long chain alkyls bonded to the nitrogen atom is a single or mixed n-alkyl containing about 8 to about 24 carbon atoms and may be the same or different if two of said long chain alkyls are so bonded, and the alkyl group bonded to a ring carbon atom of any alkylbenzyl group present contains 1 to 4 carbon atoms.

6. The composition of claim 5 wherein the active quat present consists of about 30 to about 50 wt. % of at least one long chain n-alkyl dimethyl benzyl ammonium chloride and about 50 to about 70 wt. % of at least one di(long chain n-alkyl) dimethyl ammonium chloride.

7. The composition of claim 6 wherein said active quat consists of about 40 wt. % of long chain n-alkyl (50 wt. % $C_{14}$, 40 wt. % $C_{12}$, 10 wt. % $C_{16}$) dimethyl benzyl ammonium chloride, about 30 wt. % of n-octyl n-decyl dimethyl ammonium chloride, about 15 wt. % of di-n-octyl dimethyl ammonium chloride, and about 15 wt. % of di-n-decyl dimethyl ammonium chloride.

8. The composition of claim 5 wherein the active quat present consists of about 40 to about 60 wt. % of at least one long chain n-alkyl dimethyl benzyl ammonium chloride and about 40 to about 60 wt. % of at least one long chain n-alkyl dimethyl ethylbenzyl ammonium chloride.

9. The composition of claim 8 wherein the active quat consists of about 50 wt. % of long chain n-alkyl (60 wt. % $C_{14}$, 30 wt. % $C_{16}$, 5 wt. % $C_{12}$, 5 wt. % $C_{18}$) dimethyl benzyl ammonium chloride and 50 wt. % of long chain n-alkyl (68 wt. % $C_{12}$, 32 wt. % $C_{14}$) dimethyl ethylbenzyl ammonium chloride.

10. The composition of claim 1 wherein said range of quat is from about 0.6 to about 1.0 wt. %.

11. The composition of claim 1 wherein said dilution is in the ratio of 1/32.

12. The composition of claim 1 also containing a nonionic surfactant.

13. The composition of claim 12 wherein said nonionic surfactant is an ethoxylated fatty alcohol containing $C_{10}$–$C_{18}$ alkyl groups and an average of about 1–15 moles of ethylene oxide (EO).

14. The composition of claim 13 wherein said ethoxylated fatty alcohol is a linear primary or secondary monohydric alcohol containing $C_{12}$–$C_{16}$ alkyl groups and an average of 3–12 moles of EO.

15. The composition of claim 12 wherein the amount of said nonionic surfactant is in the range of about 0.2 to about 10.0 wt. %.

16. The composition of claim 15 wherein said range of nonionic surfactant is from about 0.5 to about 2.5 wt. %.

17. The composition of claim 1 which also contains a chelating agent effective for sequestering iron ions.

18. A disinfecting cleaning composition comprising an aqueous solution of a cleansing amount of ammonia in the range of from about 1.0 to about 5.0 wt. which results in the removal of a significant amount of soils and stains when applied to a surface after appropriate dilution, an amount of at least one biocidal, non-ampholytic quarternary ammonium salt (quat), in the range of about 0.4 to about 1.6 wt. % of the total composition, and as a chelating agent effective for sequestering iron ions, the trisodium salt of N-hydroxyethylethylenediaminetriacetic acid and/or triethanolamine (TEA).

19. A disinfecting cleaning composition comprising an aqueous solution of a cleansing amount of ammonia in the range of from about 1.0 to about 5.0 wt. % which results in the removal of a significant amount of soils and stains when applied to a surface after appropriate dilution, an amount of at least one biocidal, non-ampholytic quarternary ammonium salt (quat), in the range of about 0.4 to about 1.6 wt. % of the total composition, and an alkaline bicarbonate.

20. The composition of claim 18 wherein said chelating agent comprises both said trisodium salt and said TEA each of which is present in the amount of about 0.01 to about 0.5 wt.

21. The composition of claim 19 wherein said alkaline bicarbonate is sodium bicarbonate (SBC).

22. The composition of claim 21 wherein said SBC is present in the range of about 0.1 to about 5.0 wt. %.

23. The composition of claim 22 wherein said range of SBC is from about 0.5 to about 3.0 wt. %.

24. The composition of claim 1 which contains water in the range of about 69 to about 98 wt. %.

25. The composition of claim 24 wherein said range of water is about 86 to about 97 wt. %.

26. A process of cleaning a hard surface comprising diluting the composition of claim 1 with water such that the diluted composition contains about 100 to about 1000 ppm of said quat and applying said diluted composition to said surface.

27. The process of claim 26 wherein said diluting is at a dilution ratio of about 1:16 to about 1:32.

* * * * *